(12) United States Patent
Bauta et al.

(10) Patent No.: US 7,947,824 B2
(45) Date of Patent: *May 24, 2011

(54) PROCESS FOR PREPARING PURINE NUCLEOSIDES

(75) Inventors: William E. Bauta, San Antonio, TX (US); Brian D. Burke, Lafayette, IN (US); Brian E. Schulmeier, San Antonio, TX (US); William R. Cantrell, Jr., San Antonio, TX (US); Dennis P. Lovett, San Antonio, TX (US); Jose Puente, San Antonio, TX (US)

(73) Assignee: Genzyme Corporation, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/435,326

(22) Filed: May 4, 2009

(65) Prior Publication Data

US 2009/0286971 A1    Nov. 19, 2009

Related U.S. Application Data

(63) Continuation of application No. 10/755,005, filed on Jan. 9, 2004, now Pat. No. 7,528,247, and a continuation-in-part of application No. 10/209,808, filed on Aug. 1, 2002, now Pat. No. 6,680,382.

(60) Provisional application No. 60/309,590, filed on Aug. 2, 2001.

(51) Int. Cl.
*C07H 19/16* (2006.01)
*C07H 19/073* (2006.01)

(52) U.S. Cl. ............... 536/55.3; 536/27.1; 536/27.3; 536/28.1

(58) Field of Classification Search ............ 536/27.3, 536/27.1, 55.3, 28.1
See application file for complete search history.

(56) References Cited

U.S. PATENT DOCUMENTS

| | | | |
|---|---|---|---|
| 4,751,221 A | 6/1988 | Watanabe et al. | |
| 5,106,837 A | 4/1992 | Carson et al. | |
| 5,206,351 A | 4/1993 | Markovac et al. | |
| 5,262,531 A | 11/1993 | Kawakami et al. | |
| 5,310,732 A | 5/1994 | Carson et al. | |
| 5,384,310 A * | 1/1995 | Montgomery et al. | 514/46 |
| 5,459,256 A | 10/1995 | Marquez | |
| 5,506,214 A | 4/1996 | Beutler | |
| 5,541,164 A | 7/1996 | Carson et al. | |
| 5,661,136 A | 8/1997 | Montgomery et al. | |
| 5,744,597 A | 4/1998 | Chou et al. | |
| 5,821,357 A * | 10/1998 | Chou et al. | 536/55.3 |
| 6,680,382 B2 * | 1/2004 | Bauta et al. | 536/55.3 |
| 6,949,640 B2 * | 9/2005 | Montgomery et al. | 536/27.4 |
| 7,528,247 B2 * | 5/2009 | Bauta et al. | 536/55.3 |

FOREIGN PATENT DOCUMENTS

| | | |
|---|---|---|
| EP | 0314011 A2 | 3/1989 |
| WO | WO89/08658 | 9/1989 |
| WO | 0428109 | 9/1991 |
| WO | WO95/32718 | 12/1995 |
| WO | WO01/60383 | 8/2001 |

OTHER PUBLICATIONS

The Merck Index, 1996, pp. 13, 1229 and 1035.
Howell et al., Antiviral Nucleosides. A Stereospecific, Total Synthesis of 2'-Fluoro-2'-deoxy B-D-arabinofuranosyl Nucleosides, J. Org. Chem. vol. 53, No. 1:85-88, 1988.
Obara et al., New Naplanocin Analogues. 7. Synthesis and Antiviral Activity of 2-Halo Derivatives of Naplanocin A1, J. Med. Chem., vol. 39, No. 19:3847-3852, 1996.
Carson et al., Oral antilymphocyte activity and induction of apoptosis by 2-chloro-2'-arabino-fluoro-2'-deoxyadenosine, Proc. Natl. Acad. Sci, USA, vol. 89, pp. 2970-2974, 1992.
Chu et al., Nucleosides. CXXXV. Synthesis of some 9-(2-deoxy-2-fluoro-beta-D-arabinofuranosyl)-9H-purines and their biological activities, Chemical and Pharmaceutical Bulletin,37, 2:336-339, 1989.

* cited by examiner

*Primary Examiner* — Shaojia Anna Jiang
*Assistant Examiner* — Ganapathy Krishnan
(74) *Attorney, Agent, or Firm* — Christopher J. Verni, Esq.

(57) ABSTRACT

The present invention for the stereoselective preparation of 2-deoxy-β-D-adenine nucleosides wherein a blocked 2-deoxy-α-D-arabinofuranosyl halide is coupled with the salt of an adenine derivative.

6 Claims, 4 Drawing Sheets

PROCESS FOR PREPARING PURINE NUCLEOSIDES

This application is a continuation of U.S. application Ser. No. 10/755,005, filed Jan. 9, 2004, currently pending, which is a continuation-in-part of U.S. application Ser No. 10/209,808, filed Jul. 31, 2002, now U.S. Pat. No. 6,680,382, which in turn claims priority to U.S. provisional application Ser. No. 60/309,590, filed Aug. 2, 2001, the contents of all of which are hereby incorporated by reference.

The claimed inventions were made by, on behalf of, and/or in connection with: (i) a joint research agreement between Southern Research Institute and Bioenvision, Inc., (f/k/a Eurobiotech Group, Inc.), now part of Genzyme Corporation, and (ii) a joint research agreement between Bioenvision, Inc. and Ilex Oncology, Inc., now part of Genzyme Corporation. The agreements were in effect on or before the date the claimed inventions were made, and the claimed inventions were made as a result of activities undertaken within the scope of the agreement.

FIELD OF THE INVENTION

The present invention relates generally to the chemical preparation of purine nucleosides. More specifically, the invention relates to the coupling of an adenine derivative with a blocked arabinofuranosyl to form a β-D-adenine nucleoside derivative. Such nucleosides are valuable compounds in the field of cancer therapy and as anti-viral agents.

BACKGROUND OF THE INVENTION

A number of β-D-purine nucleosides derived from adenine are useful as antitumor and antiviral agents. An important step in the synthesis of such agents is the formation of the N-glycoside bond between the adenine nucleobase and an arabinofuranosyl derivative. The coupling reactions used to form the N-glycoside bond of 2'-deoxynucleosides have typically resulted in the formation of a mixture of α and β-anomers.

Nucleosides have been synthesized by fusion glycosylation, wherein the reaction is carried out in the absence of solvent at a temperature sufficient to convert the reactants to a molten phase. E.g., 2,6-dichloropurine has been coupled under fusion conditions with 5-O-benzyl-2-deoxy-1,3-di-O-acetyl-2-fluoroarabinose to form a 2'-fluoroarabinonucleoside in 27% yield (Wright et al., J. Org. Chem. 34:2632, 1969). Another synthetic method utilizes silylated nucleobase derivatives, e.g., a silylated nucleobase has been coupled with a peracetylated deoxy-sugar in the presence of a solvent and a Friedel Crafts catalyst (Vorbruggen et al., J. Org. Chem. 41: 2084, 1976). This method has been modified by incorporating a sulfonate leaving group in the deoxy-sugar in the synthesis of 2'-deoxy-2'-difluoronucleosides (U.S. Pat. Nos. 4,526,988; 4,965,374).

High yields of 2'-deoxy-2'-fluoro-pyrimidine nucleosides were obtained from refluxing pyrimidines with 2-deoxy-2-fluoro-3,5-di-O-benzoyl-α-O-arabinofuranosyl bromide. (Howell et al., J. Org. Chem. 53:85-88, 1988). It was found that use of solvents with lower dielectric constants produced have higher β:α anomer ratios. It was postulated that such solvents favored an $S_N2$ reaction, whereas solvents with higher dielectric constants favored production of α-anomers via an ionic $S_N1$ pathway.

Anion glycosylation procedures have also been used to prepare 2'-deoxy-2'-fluoropurine nucleosides. EP 428109 discloses the coupling of the sodium salt of 6-chloropurine, formed by sodium hydride, with 3,5-dibenzyl-α-D-arabinofuranosyl bromide using conditions that favor $S_N2$ displacement. Use of 1:1 acetonitrile/methylene chloride resulted in a nucleoside product with a β:α anomer ratio 10:1, as opposed to a ratio of 3.4:1 observed when using a silylated purine reactant. In regard to the use of adenine salts, the amino substituent at the C-6 position was protected as a benzoyl derivative during the coupling reaction. Protecting the exocyclic amino group precludes the formation of arabinofuranosyl adducts which otherwise may be expected to be produced (e.g., Ubukata et al., Tetrahedron Lett., 27:3907-3908, 1986; Ubukata et al., Agric. Biol. Chem., 52: 1117-1122, 1988; Searle et al., J. Org. Chem., 60:4296-4298, 1995; Baraldi et al., J. Med. Chem., 41:3174-3185, 1998). The preparation of α and β anomers of 2'-deoxy-2'-fluoropurine and 2'-difluoropurine nucleosides by anion glycosylation are disclosed by U.S. Pat. Nos. 5,744,597 and 5,281,357, with β-anomer enriched nucleosides prepared in a β:α anomer ratio of greater than 1:1 to about 10:1 and from greater that 1:1 to about 7:1 respectively. In regard to purines substituted with exocyclic amino groups, both patents again disclose protecting such groups during coupling to an appropriate sugar moiety. U.S. Pat. No. 5,281,357 also discloses the effect of solvents on the β:α anomer ratio of 9-[1-(2'-deoxy-2',2'-difluoro-3',5'-di-O-benzoyl-D-ribofuranosyl)]-2,6-dipivalamidopurine prepared by coupling the potassium salt of 2,6-dipivalamidopurine with an α anomer enriched preparation of 2-deoxy-2,2-difluoro-D-ribofuranosyl-3,5-dibenzoyl-1-trifluoromethanesulfonate. There was no correlation between the dielectric constant of the six solvents used and the β:α anomer ratio, e.g. ethyl acetate and acetonitrile both gave the same ratio of 1.6:1. t-Butyl alcohol gave the highest β:α anomer ratio of 3.5:1.

Despite the preparative methods for purine nucleosides known in the art, there is still a need for economically preferable, effective and efficient process for the preparation of these compounds. The object of the present invention is to provide such a process. Further objects are to minimize the number of process reaction steps and to provide a process that is readily scalable for the production of commercial-scale quantities. Other objects and advantages will become apparent to persons skilled in the art and familiar with the background references from a careful reading of this specification.

SUMMARY OF THE INVENTION

In its most general terms, one aspect of the present invention provides for the preparation of β-adenine nucleosides by coupling an adenine derivative containing an unprotected exocyclic amino group at the C-6 position, and a blocked arabinofuranosyl derivative. In preferred embodiments, this reaction can be depicted as:

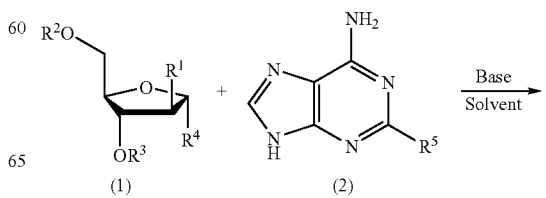

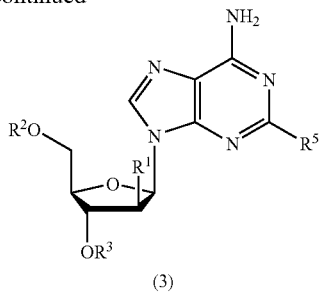

(3)

$R^1$ is hydrogen, halogen or —$OR^6$, wherein $R^6$ is a hydroxy protecting group. In a preferred embodiment $R^1$ is fluoro. $R^2$ and $R^3$ are hydroxy-protecting groups. In preferred embodiments $R^2$, $R^3$ and $R^6$ are independently benzoyl or acetyl. $R^4$ is a leaving group. Suitable leaving groups include, halo, fluorosulfonyl, alkylsulfonyloxy, trifluoroalkylsulfonyloxy and arylsulfonyloxy. In a preferred embodiment, $R^4$ is bromo. $R^5$ is hydrogen, halogen or —$NH_2$. In preferred embodiments, $R^5$ is chloro or fluoro.

Surprisingly, this reaction proceeds without substantial production of adducts resulting from addition of the blocked arabinofuranosyl (1) with the exocyclic amino group at the C-6 position of compound (2) (hereinafter termed "C-6 exocyclic amino group"), which remains unprotected during the reaction, and/or the nitrogen at the N-7 position of the adenine ring. An example of an undesired C-6 exocyclic amino group by-product adduct is represented by the following formula:

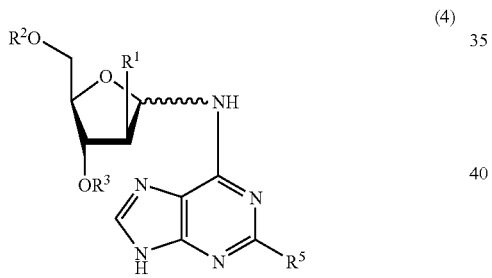

(4)

For the purposes of the present invention, and in light of the objective to provide an economically preferable, effective and efficient process, "substantial formation" means conversion of about 40% of the adenine derivative of formula (2) to a by-product adduct or adducts resulting from addition of the blocked arabinofuranosyl of formula (1) to the unprotected C-6 exocyclic amino group and/or N-7 position of compound (2). In embodiments wherein $R^5$ is —$NH_2$ (hereinafter termed "$R^5$—$NH_2$ group"), "substantial formation" means conversion of about 40% of the adenine derivative of formula (2) to by-product adduct(s) resulting from addition of the blocked arabinofuranosyl of formula (1) to the unprotected C-6 exocyclic amino group and/or N-7 position and/or the $R^5$—$NH_2$ group of compound (2).

Even more surprising is that the reaction can proceed without even a significant production of adducts resulting from addition of the blocked arabinofuranosyl (1) with the C-6 exocyclic amino group and/or N-7 position of compound (2). For the purposes of the present invention, "significant production" means conversion of about 5% of the adenine derivative of formula (2) to a by-product adduct or adducts resulting from addition of the blocked arabinofuranosyl (1) to the unprotected C-6 exocyclic amino group and/or N-7 position of compound (2). In embodiments wherein $R^5$ is —$NH_2$, "significant production" means conversion of about 5% of the adenine derivative of formula (2) to a by-product adduct(s) resulting from addition of the blocked arabinofuranosyl of formula (1) to the unprotected C-6 exocyclic amino group and/or N-7 position and/or the $R^5$—$NH_2$ group of compound (2).

Useful bases are generally those with a pKa in water of 15 or greater. In preferred embodiments, the base is an alkali metal base with a pKa in water of 17 or above, more preferred being a potassium base. In preferred embodiments, the base is a sterically hindered base, e.g., potassium t-butoxide or potassium t-amylate. Suitable inert solvents include, but are not limited to, t-butyl alcohol, acetonitrile, dichloromethane, dichloroethane, t-amyl alcohol, tetrahydrofuran or mixtures thereof. In preferred embodiments, the solvent or solvent mixture has a boiling point of about 80° C. or greater.

The process of the present invention also further comprises de-protection of the blocked carbohydrate moiety to form a β-nucleoside of the formula:

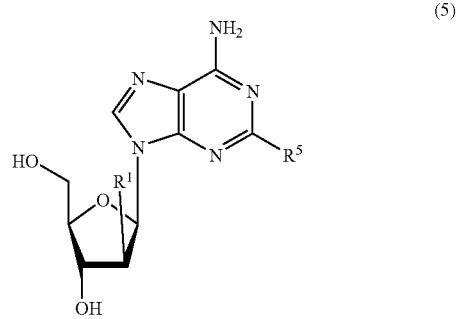

(5)

wherein, $R^1$ and $R^5$ are as defined above.

In some embodiments, the adenine derivative is 2-chloroadenine and the blocked arabinofuranosyl derivative is a 2-deoxy-2-fluoro-arabinofuranosyl derivative, whereupon the resulting β-nucleoside is a 2-chloro-9-(2'-deoxy-2'-fluoro-β-D-arabinofuranosyl)adenine derivative. The reaction can be depicted as:

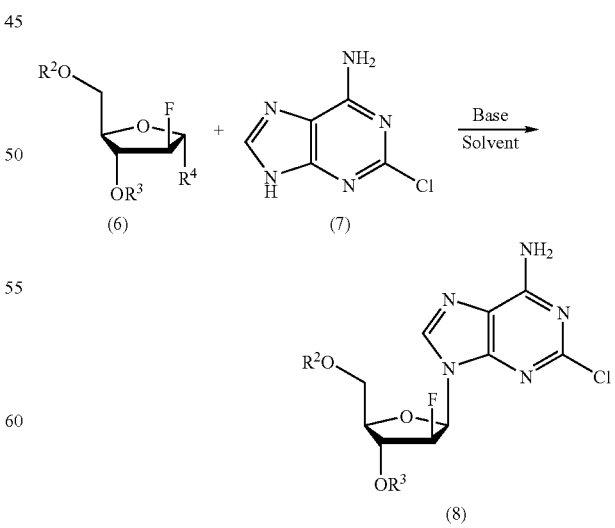

wherein $R^2$, $R^3$ and $R^4$ are as defined above. The process also further comprises de-protecting the carbohydrate moiety to form 2-chloro-9-(2'-deoxy-2'-fluoro-β-D-arabinofuranosyl) adenine, also known as clofarabine.

Another aspect of the invention is the discovery of the surprising stereoselectivity that can be achieved in the production 2'-deoxy-2'-halo-β-D-adenine nucleosides wherein such nucleosides are also produced in high yield. This reaction can be depicted as:

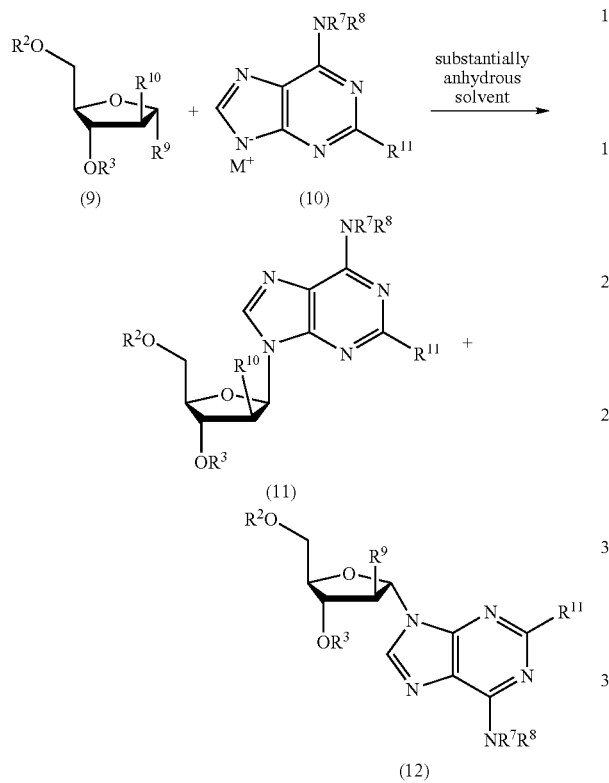

$R^7$ and $R^8$ are independently hydrogen, $C_1$-$C_4$ alkyl, or a protecting group, $R^9$ and $R^{10}$ are independently halogen, $M^+$ is potassium, $R^{11}$ is halogen or —$NR^7R^8$, wherein $R^7$ and $R^8$ are as described above, and $R^2$ and $R^3$ are as defined above. Halogen includes bromo, fluoro, chloro and iodo. In a preferred embodiment $R^{10}$ is fluoro. In various embodiments $R^9$ is chloro or, preferably, bromo. In preferred embodiments, $R^7$ and $R^8$ are independently hydrogen, acyl, such as acetyl or benzoyl, or silyl, such as trimethylsilyl. In some embodiments, the process further comprises the addition of calcium hydride. Suitable substantially anhydrous inert solvents include t-butyl alcohol, acetonitrile, dichloromethane, dichloroethane, t-amyl alcohol, tetrahydrofuran or mixtures thereof. In preferred embodiments, the substantially anhydrous solvent is a mixture of t-butyl alcohol and acetonitrile, or a mixture of t-butyl alcohol and dichloroethane, or a mixture of dichloroethane and acetonitrile, or a mixture of t-amyl alcohol and dichloroethane, or a mixture of t-amyl alcohol and acetonitrile, or a mixture of t-amyl alcohol, acetonitrile and dichloromethane, or a mixture of t-amyl alcohol, acetonitrile and dichloroethane. In preferred embodiments, the substantially anhydrous solvent has a boiling point of about 80° C. or greater.

In some embodiments, the adenine derivative salt (10) is formed in situ by the reaction of a potassium base with the corresponding adenine derivative. In some embodiments the potassium base has a pKa in water of 15 or greater and in preferred embodiments the potassium base is a hindered base with a pKa in water of 17 or greater, such as potassium t-butoxide or potassium t-amylate.

In preferred embodiments the reaction mixture is heterogenous in that either: (1) the adenine salt, if added directly to the reaction mixture; or (2) the adenine base, if adenine salt is formed in situ in the reaction mixture, is not totally soluble in the substantially anhydrous solvent.

In various embodiments of the invention, the coupling reaction produces in the substantially anhydrous solvent reaction mixture, without further purification or isolation, a preparation wherein the ratio of the β-anomer of formula (11) to the α-anomer of formula (12) is at least about 10:1, or preferably is at least about 15:1, or more preferable is at least about 20:1. Thus, the anomer ratio may be 10:1 or greater, 15:1 or greater or 20:1 or greater. In preferred embodiments the β-anomer of formula (11) is prepared in a yield of about 40% or greater. In more preferred embodiments, the β-anomer of formula (11) is prepared in yields of about 50% or greater or about 80% or greater.

The process of the present invention may also further comprises isolation of the α-anomer (11) by subjecting the mixture of β and α-anomers to recrystallization or by a re-slurry procedure. In a preferred embodiment, the further purification comprises reslurry from methanol or crystallization from a mixture of butyl acetate and heptane. In various embodiments, the purified preparation comprises a mixture of nucleosides wherein the ratio of the β-anomer of formula (11) to the α-anomer of formula (12) is at least about 20:1, or least about 40:1, or at least about 60:1.

The process also further comprises de-protection of the blocked carbohydrate moiety of the protected β-anomer to form a β-nucleoside of the formula:

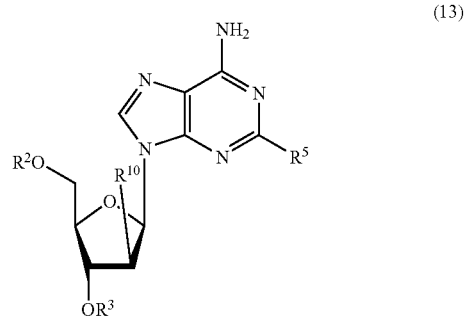

wherein, $R^5$ and $R^{10}$ are as defined above. When $R^5$ is chloro and $R^8$ is fluoro, the unblocked β-nucleoside of formula (13) is 2-chloro-9-(2'-deoxy-2'-fluoro-β-D-arabinofuranosyl)adenine. The deprotection process including the associated work-up of the product may result in a ratio of the β-anomer of formula (11) to the α-anomer of formula (12) that is at least about 99:1 or greater, or about 400:1 or greater, or about 500:1 or greater, or about 1000:1 or greater.

Another aspect of the present invention is a multi-step process for the preparation of a composition comprising 2-chloro-9-(2'-deoxy-2'-fluoro-β-D-arabinofuranosyl)adenine. This comprises the integration of the other aspects of the present invention into an economically preferable, effective and efficient synthesis and isolation of 2-chloro-9-(2'-deoxy-2'-fluoro-β-D-arabinofuranosyl)adenine. This process minimizes the number of steps in part by not requiring protection of the C-6 exocyclic amino group. In addition, the surprising stereoselective preference for the β-anomer in part enables the preparation of a composition with an β:α anomer ratio of at least 99:1 or in preferred embodiments is about 400:1 or greater, about 500:1 or greater or about 1000:1 or greater, without utilizing a preparative chromatography step for the purification of the β-anomer. The absence of a chromatographic step is a major advantage in regard to an economically preferable commercial-scale process.

The process comprises reacting 3,5-O-dibenzoyl-2-deoxy-2-fluoro-α-D-arabinofuranosyl bromide with a 2-chloroadenine potassium salt of the formula:

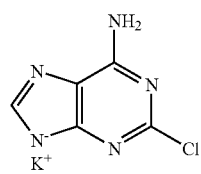

(14)

in the presence of a substantially anhydrous solvent to form 2-chloro-9-(3',5'-O-dibenzoyl-2'-deoxy-2'-fluoro-β-D-arabinofuranosyl)adenine. The C-6 exocyclic amino group of the 2-chloroadenine potassium salt is not protected during the process. The 2-chloro-9-(3',5'-O-dibenzoyl-2'-deoxy-2'-fluoro-β-D-arabinofuranosyl)adenine is then de-protected to form 2-chloro-9-(2'-deoxy-2'-fluoro-β-D-arabinofuranosyl)adenine, which is then isolated to provide a composition comprising 2-chloro-9-(2'-deoxy-2'-fluoro-β-D-arabinofuranosyl)adenine. In some embodiments, wherein the composition produced by the multi-step process, as described above, also comprises 2-chloro-9-(2'-deoxy-2'-fluoro-α-D-arabinofuranosyl)adenine, the 2-chloro-9-(2'-deoxy-2'-fluoro-α-D-arabinofuranosyl)adenine is substantially pure. For the purposes of the present invention, substantially pure 2-chloro-9-(2'-deoxy-2'-fluoro-α-D-arabinofuranosyl)adenine means that the ratio of β-anomer to α-anomer as measured by high pressure liquid chromatography and spectrophotometric analysis, is at least 99:1.

The process may further comprise isolating the 2-chloro-9-(3',5'-O-dibenzoyl-2'-deoxy-2'-fluoro-β-D-arabinofuranosyl)adenine before the deprotection step. In some embodiments, this isolation may comprise reslurry and/or recrystallization, which may be effected by use of methanol or by use of a mixture of butyl acetate and heptane. In other embodiments, the isolation of 2-chloro-9-(2'-deoxy-2'-fluoro-β-D-arabinofuranosyl)adenine also comprises recrystallization. In some embodiments, the recrystallization is from methanol.

In some embodiments, the 2-chloroadenine potassium salt is prepared in situ by the reaction of a potassium base with 2-chloroadenine in a suitable substantially anhydrous inert solvent. In preferred embodiments, the base is potassium t-butoxide or potassium t-amylate. Suitable inert solvents include t-butyl alcohol, acetonitrile, dichloromethane, dichloroethane, t-amyl alcohol, tetrahydrofuran or mixtures thereof. In preferred embodiments, the substantially anhydrous solvent is a mixture of t-butyl alcohol and acetonitrile, or a mixture of t-butyl alcohol and dichloroethane, or a mixture of dichloroethane and acetonitrile, or a mixture of t-amyl alcohol and dichloroethane, or a mixture of t-amyl alcohol and acetonitrile, or a mixture of t-amyl alcohol, acetonitrile and dichloromethane, or a mixture of t-amyl alcohol, acetonitrile and dichloroethane.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
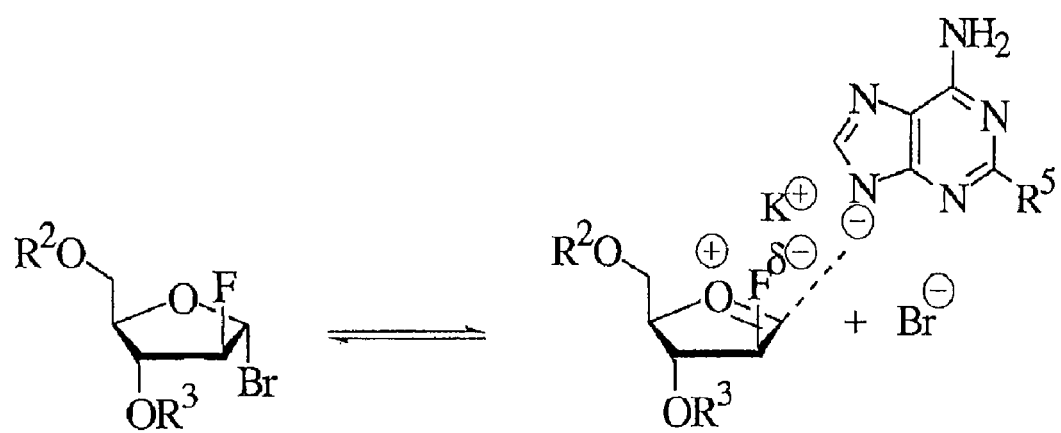
FIG. 1—Schematic representing potential rationale for the effect of potassium in the stereoselective production of 2'-deoxy-2'-fluoro-β-D-adenine nucleosides. $R^2$, $R^3$ and $R^5$ are as defined in the Description.

1. Coupling Reactions Utilizing Purine Bases with Unprotected Exocyclic Amino Groups One aspect of the present invention provides for the preparation β-adenine nucleosides by coupling an adenine derivative with an unprotected C-6 exocyclic amino group and a blocked arabinofuranosyl derivative, in the presence of a base and solvent. The blocked arabinofuranosyl derivative may be depicted by the structure:

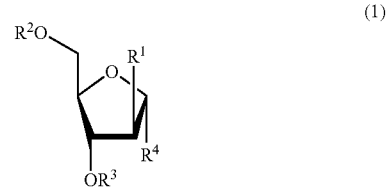

(1)

$R^1$ is hydrogen, halogen or —$OR^6$, wherein $R^6$ is a hydroxy protecting group. Halogens include bromo, chloro, fluoro and iodo. $R^2$ and $R^3$ are hydroxy protecting groups. Hydroxy protecting groups are known in the art as chemical functional groups that can be selectively appended to and removed from a hydroxy functionality present in a chemical compound to render such functionality inert to chemical reaction conditions to which the compound is exposed. Hydroxy protecting groups are described in Greene and Wuts, Protective Groups in Organic Synthesis, 2d edition, John Wiley & Sons, New York, 1991, and include formyl, acetyl, propionyl, arylacyl (e.g., benzoyl or substituted benzoyl), trityl or monomethoxytrityl, benzyl or substituted benzyl, carbonate derivatives (e.g., phenoxycarbonyl, ethoxycarbonyl and t-butoxycarbonyl), and trisubstituted silyl, including trialkylsilyl (e.g. dimethyl-t-butylsilyl) or diphenylmethylsilyl. In preferred embodiments, the protecting groups are independently benzoyl or acetyl.

$R^4$ is a leaving group, suitable examples of which include halogen, alkylsulfonyloxy, and arylsulfonyloxy. Halogens include chloro, fluoro, iodo and, in a preferred embodiment, bromo. Blocked α-arabinofuranosyl halides can be prepared by various methods known in the art employing standard procedures commonly used by one of skill in the art, e.g., 3,5-O-dibenzoyl-2-deoxy-2-fluoro-α-D-arabinofuranosyl bromide (exemplified in Example 1; Tann et al., J. Org. Chem., 50:3644, 1985, herein incorporated by reference);

3-O-acetyl-5-O-benzyl-2-deoxy-2-fluoro-α-D-arabinofuranosyl bromide (Fox et al., Carbohydrate Res., 42:233, 1975, herein incorporated by reference); 2,3,5-O-tribenzyl-α-D-arabinofuranosyl chloride (U.S. Pat. No. 5,110,919, herein incorporated by reference); and 3,5-O-di-p-toluoyl-2-deoxy-α-arabinofuranosyl chloride (Bhattacharya et al., J. Org. Chem., 28:428 1963; Nuhn et al., Pharmazie, 24:237, 1969, both herein incorporated by reference). Preparation of blocked α-arabinofuranosyl derivatives substituted at the C-1 position with alkylsulfonates and arylsulfonates are disclosed in U.S. Pat. Nos. 5,401,861 and 5,744,579, both herein incorporated by reference. Alkyl sulfonates include methanesulfonate, ethylsulfonate and butylsulfonate and substituted alkyl sulfonates include compounds such as trifluoromethane sulfonate and 1,1,1-trifluoromethanesulfonate. Arylsulfonates includes substituted arylsulfonates such as p-nitrobenzenesulfonate, p-bromobenzenesulfonate, p-methylbenzesulfonate, and the like.

Useful bases generally have a pKa in water of 15 or greater and are suitable for the formation of a salt of the adenine derivative (2), as depicted by the formula:

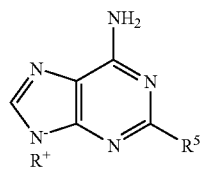

(15)

$R^5$ is as defined previously and $R^+$ is a monovalent cation. The base may be an alkali metal base, and in preferred embodiments the alkali metal base is a potassium base. In preferred embodiments, the base is a sterically hindered base, e.g., potassium t-butoxide or potassium t-amylate.

Solvents useful in the present invention are those that are inert in respect to the reaction. Suitable inert solvent include, but are not limited to, t-butyl alcohol, acetonitrile, dichloromethane, dichloroethane, t-amyl alcohol, tetrahydrofuran or mixtures thereof.

In a preferred embodiment, the reaction is carried out at room temperature. However, in other embodiments the reaction is carried out at elevated or lower temperatures. E.g., the reaction can be carried out at about 40° C., or about 50° C., or about 60° C., or under reflux conditions. Alternatively the reaction can be carried out from about −25° C. to about 25° C., e.g., at about −20° C. or at about −10° C., or at about 0° C., or at about 10° C.

Wherein an amino group is described as "unprotected," this means that the amino group has not been blocked by an amino protecting group. The use and types of amino protecting functionalities are well known in the art. Examples are described in Greene and Wuts, *Protective Groups in Organic Synthesis,* 2d edition, John Wiley & Sons, New York, 1991.

The molar ratio of reactants is not considered to be critical and in preferred embodiments approximately equal molar equivalents of blocked arabinofuranosyl derivative (1), adenine derivative (2) and base are used. In some embodiments, a slight molar excess (e.g., 1.05 to 1.15 equivalents) of adenine derivative (2) and/or base are used. The preferred order and manner of addition for any specific embodiment can be determined by routine experimentation with a view towards both reaction performance and chemical engineering and productions considerations.

2. Stereoselective Preparation of 2-Deoxy-Purine Nucleosides

Another aspect of the invention is the stereoselective preparation of 2-deoxy-β-D-adenine nucleosides. In this process, a blocked 2-deoxy-α-D-arabinofuranosyl halide is coupled with the salt of an adenine derivative depicted by the formula:

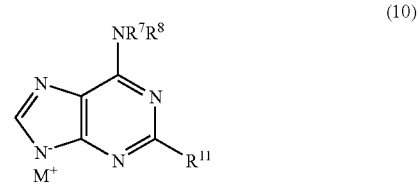

(10)

wherein $R^7$, $R^8$, $R^{11}$ and $M^+$ are as previously described. Surprisingly, the identity of the cation has a profound effect on the stereoselectivity of the coupling reaction. Potassium salts produced larger β:α anomer ratios than lithium or sodium salts. The salt depicted by formula (10) can be produced in situ by use of potassium bases and the corresponding adenine derivatives. Suitable bases generally have a pKa in water of 15 or greater and include potassium t-alkoxide bases, potassium hydroxide and hindered bases include potassium diisopropylamide, potassium bis(trimethylsilyl)amide, potassium hexamethyldisilazide, potassium hydride and the like. In preferred embodiments, the base is a sterically hindered base with a pKa in water of 17 or above, e.g., potassium t-butoxide or potassium t-amylate. The stronger bases are preferred in that they enhance the production of the potassium salt of the purine and also because there is in general a reciprocal relationship between the strength of a base and nucelophilicty, and in that regard stronger bases have less of a propensity to displace the C1 halide of the sugar reactant. Hinder bases are preferred, at least in part, for a similar rationale, in that hindered bases have less of a propensity than non-hindered bases to act as a nucleophile. In addition, bases such as potassium t-butoxide and potassium t-amylate, produce the corresponding alcohols during the reaction, solvents that do not have detrimental effect on the reaction and may have a beneficial effect on the reaction. In contrast, bases such as potassium hydroxide produce water during the reaction, which as stated below, has a potentially detrimental effect on the reaction.

While not being bound by any theory, the preferential stereoselectivity observed with potassium may be due, e.g., when $R^{10}$ is fluoro and $R^9$ is bromo, to an electrostatic attraction between the electronegative fluorine atom and the hard potassium cation, leading to a preferential β-face attack, as depicted in FIG. 1. The lack of selectivity of lithium and sodium may be due to a more covalent association of the cation with the purine base. The present invention also encompasses other cations, such as cesium, that can replace potassium as a hard cation.

The solvent employed also has a marked effect on the β:α anomer ratio. Generally solvents with a lower dielectric constant favor production of the β anomer. But solvent choice is not dictated simply by dielectric constant, in that there is a tendency for an inverse relationship between increasing the β:α anomer ratio and the yield of the β and α anomers. This effect presumably relates to the solubility of reactants and/or intermediates. In this regard, in preferred embodiments, the reaction is heterogenous, meaning in the context either: (1) the adenine salt, if added directly to the reaction mixture; or (2) the adenine base, if adenine salt is formed in situ in the reaction mixture, is not totally soluble in the substantially anhydrous solvent. These conditions favor combinations of desirable β:α anomer ratios and yields. Suitable solvents include t-butyl alcohol, acetonitrile, dichloromethane, dichloroethane, t-amyl alcohol, isoamyl alcohol, tetrahydrofuran or mixtures thereof. In preferred embodiments, the solvent is a mixture of t-butyl alcohol and acetonitrile, or a mixture of t-butyl alcohol and dichloroethane, or a mixture of dichloroethane and acetonitrile, or a mixture of t-amyl alcohol and dichloroethane, or a mixture of t-amyl alcohol and acetonitrile, or a mixture of t-amyl alcohol, acetonitrile and dichloromethane, or a mixture of t-amyl alcohol, acetonitrile and dichloroethane. Two component mixtures the two solvents may be combined in the range of about 1:4 to about 1:1 v/v. In three component mixtures, the three solvents may be combined in ratios of about 2:2:1, or about 2:1:1, or about 1:1:1. In preferred embodiments the solvents are substantially anhydrous as water has been found to be detrimental to the desired high β:α anomer ratio. Without being bound to any particular theory, it has believed that the water coordinates to the potassium cation thereby interfere with the proposed electrostatic interaction between the hard C-2 fluorine atom of the sugar and the hard potassium cation. Substantially anhydrous solvents may be prepared by predrying solvents, e.g., by use of calcium hydride, for use with strong hindered bases such as potassium t-butoxide and potassium t-amylate. For use of bases, such as potassium hydroxide, that produce water, a drying agent, such as calcium hydride, is preferentially present during the reaction to maintain the substantially anhydrous nature of the solvent. Thus in various embodiments, drying agents such as calcium hydride may be used to predry solvents and/or may be present in the reaction.

In a preferred embodiment, the reaction is carried out at room temperature. In other embodiments, elevated or lower temperatures are used. Lowering the temperature of the reaction, such as in the range of from room temperature to about −25° C., may lead to an increase the β:α anomer ratio. Elevated temperatures can be used in the range from room temperature to reflux conditions.

The molar ratio of reactants is not considered to be critical and in preferred embodiments when the adenine derivative salt (10) is produced in situ, approximately equal molar equivalents of blocked arabinofuranosyl derivative (9), the corresponding adenine derivative, base and, when added, calcium hydride are used. In some embodiments, a slight molar excess (e.g., 1.05 to 1.15 equivalents) of the corresponding adenine derivative and/or base are used. The preferred order and manner of addition for any specific embodiment can be determined by routine experimentation with a view towards both reaction performance and chemical engineering and productions considerations.

EXAMPLES OF THE INVENTION

Without further elaboration, it is believed that one skilled in the art can, using the preceding description, utilize the present invention to its fullest extent. The following specific examples are intended merely to illustrate the invention and not to limit the scope of the disclosure or the scope of the claims in any way whatsoever.

Example 1

Preparation of 3,5-O-Dibenzoyl-2-deoxy-2-fluoro-α-D-arabinofuranosyl Bromide

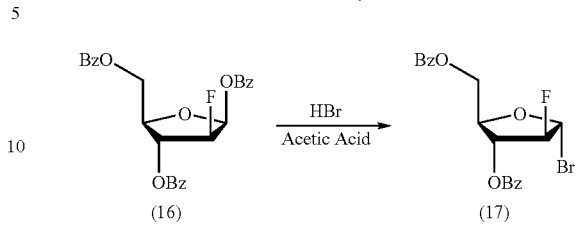

A 1-neck round bottom flask (100 mL) was equipped with a stir bar and nitrogen inlet adapter. The flask was charged with dichloromethane (10.4 mL) and 1,3,5-O-tribenzoyl 2-deoxy-2-fluoro-β-D-arabinofuranosyl (16) (2.6 gm, Sigma, St. Louis, Mo.) at room temperature. The solution was placed under nitrogen. A 33% solution of hydrogen bromide in acetic acid (0.96 gm) was charged and the resultant mixture stirred for 18 hr. The solvent was removed by rotary evaporation to give an orange residue. This was dissolved in dichloro methane (30 mL) and quenched with sodium bicarbonate brine (30 mL), whereupon the pH was 7-8. The organic phase was partitioned and washed with sodium chloride brine (30 mL). The organic phase was dried over $MgSO_4$ and filtered. Solvent removal by rotary evaporation and high vacuum afforded 3,5-O-dibenzoyl-2-deoxy-2-fluoro-α-D-arabinofuranosyl bromide (17) as a viscous yellow gum.

Example 2

Preparation of 2-Chloro-9-(3,5-O-dibenzoyl-2-deoxy-2-fluoro-β-D-arabinofuranosyl)adenine

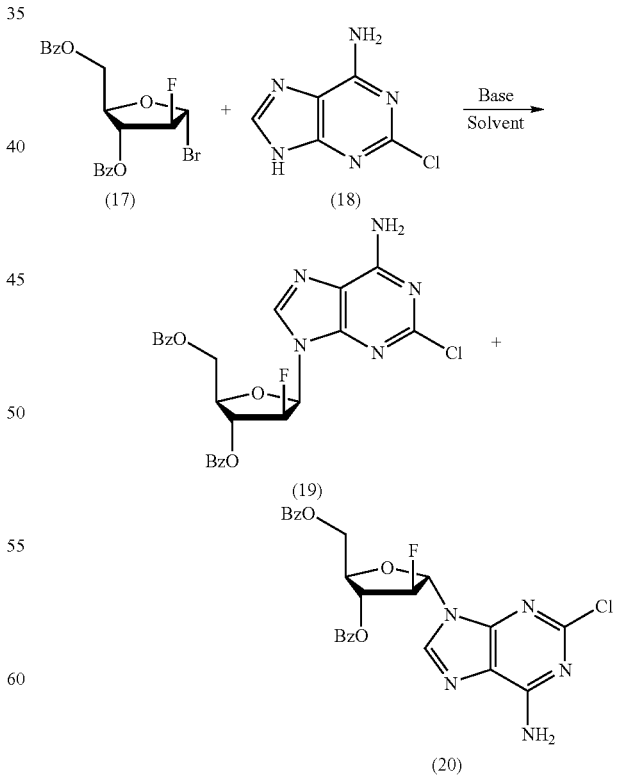

2-Chloro-9-(3,5-O-dibenzoyl-2-deoxy-2-fluoro-β-D-arabinofuranosyl)adenine (19) (Borregaard) was prepared utilizing different bases and numerous solvent systems and the optional addition of calcium hydride. In the following exemplifications, three preparations are described in detail and other preparations are summarized in Table 1.

A. Preparation I

A three neck round bottom flask was equipped with a temperature controller, nitrogen inlet and outlet tubes, septa and a magnetic stir bar. Chloroadenine (18) (0.45 g) was charged as a solid under nitrogen, followed by potassium t-butoxide (0.34 g), acetonitrile (2.3 mL) and t-butyl alcohol (6.9 mL). After stirring for 1 hour at 24° C.-26° C., 3,5-O-dibenzoyl-2-deoxy-2-fluoro-α-D-arabinofuranosyl bromide (17) (1.21 gm) was added. The resulting orange suspension was stirred at 24° C.-26° C. for 16 hours. HPLC analysis of an in-process control sample showed a 96.6% conversion and a 10.7:1 ratio of β-anomers (19) to α-anomer (20). HPLC analysis utilized a reverse phase system with a Zorbax-SB-C18 column and a mobile phase of 80:20 acetonitrile/water with 15% v/v trifluoroacetic acid at a flow rate of 1 mL/min. at 30° C. Detection was by spectrophotometric analysis at 263 nm. Conversion is expressed as area under the curve (a.u.c.) values of (19)+(20)/(18)+(19)+(20)×100. The solvent was evaporated to afford 1.79 g of an orange residue. To this was added ethyl acetate (34 mL) and the mixture stirred at ambient temperature for 1.25 hr and then filtered through filter paper and the paper rinsed twice with 5 mL of ethyl acetate. Evaporation of the filtrate solution afforded 1.28 g of light orange crystals (86.8% by HPLC area of the combined anomers). This material still contained a small amount of 2-chloroadenine (13) by HPLC. The anomeric ratio was 11.8:1. The crystals were dissolved with 33 mL ethyl acetate at ambient temperature to afford a slightly opaque solution. This was filtered through filtered through a Celite pad and the filtrate evaporated to afford 1.16 g of crystals. This material still contained a small amount of (13). The problem was remedied by more efficient filtration. The crystals were dissolved in 25 mL ethyl acetate overnight at ambient temperature to give a slightly cloudy solution. This was filtered through a Whatman 0.45 mM nylon syringe filter and evaporated to afford 1.13 g. This material contained no (18) by HPLC analysis and had an anomeric ratio of 11.9:1 and a yield of 83% with a purity of 98.1% (a.u.c.). Considering the production of anomers (19) and (20), there was no substantial formation of a by-product adduct formed by reaction of 3,5-O-dibenzoyl-2-deoxy-2-fluoro-α-D-arabinofuranosyl bromide (17) with the unprotected exocyclic amino group of 2-chloroadenine (18). In addition, HPLC analysis revealed no substantial formation of by-products.

B. Preparation II

A 3-neck round bottom flask was equipped with a magnetic stir bar, temperature controller, and nitrogen inlet line and charged with 2-chloroadenine (18) (0.29 g), followed by acetonitrile (1.6 mL), t-amyl alcohol (3.3 mL), potassium tert-butoxide (0.2 g) and calcium hydride (0.069 g). This mixture was stirred at 25° C. for 30 minutes before 3,5-O-dibenzoyl-2-deoxy-2-fluoro-α-D-arabinofuranosyl bromide (17) (0.68 g gm) dissolved in dichloromethane (3.25 mL) was charged. The orange solution was stirred for two days whereupon HPLC analysis showed a β:α anomeric ratio of 18.8:1 and a conversion of approximately 67%. Heating at 40° C. for approximately 4.5 hr resulted in a β:α anomer ratio of 18.7:1 and a decrease in the apparent conversion to 63%. The reaction mixture was vacuum filtered and the filter cake washed with dichloromethane (2×12 mL). The filtrate was passed through a nylon syringe filter and then concentrated by rotary evaporation and high vacuum pumping to afford 0.72 g of material with a β:α anomeric ratio of 19:1 and was 88% pure by HPLC (a.u.c.), giving a yield of the anomers (19) and (20) of 77%. In that there was an approximately 77% conversion of the chloroadenine, there was neither substantial nor significant formation of a by-product adduct formed by reaction of 3,5-O-dibenzoyl-2-deoxy-2-fluoro-α-D-arabinofuranosyl bromide (17) with the unprotected exocyclic amino group of 2-chloroadenine (18). In addition, HPLC analysis revealed no substantial nor significant formation of by-products.

C. Preparation III

A 3-neck 100 ml round-bottomed flask equipped with magnetic stir bar, temperature controller, and nitrogen inlet line and charged with 2:1 t-amyl alcohol:acetonitrile (9 mL) followed by 2-chloroadenine (18) (0.63 g), potassium t-amylate (0.47 g) and calcium hydride (0.15 g). This mixture was stirred at room temperature for 30 minutes before the addition of 3,5-O-dibenzoyl-2-deoxy-2-fluoro-α-D-arabinofuranosyl bromide (17) (1.5 gm) dissolved in 2:1 t-amyl alcohol:acetonitrile (7 mL). The solution was stirred for 17 hr. whereupon analysis by HPLC showed the conversion to be approximately 79% and a β:α anomer ratio of 14.5:1. The reaction mixture was vacuum filtered and the residue washed with 2×5 mL acetonitrile. The filtrate was re-filtered through a 0.45µ nylon filter and then concentrated. The concentrate residue was dissolved in butyl acetate (5 mL). Heptane (35 mL) was added and the resulting crystals were collected by vacuum filtration and subjected to a high vacuum. HPLC analysis of the crystals indicated a β:α anomer ratio of 19.4:1 and a 63% yield of material with a 90% purity (a.u.c.). In that there was an approximately 79% conversion of the chloroadenine, there was no substantial formation of a by-product adduct formed by reaction of 3,5-O-dibenzoyl-2-deoxy-2-fluoro-α-D-arabinofuranosyl bromide (17) with the unprotected exocyclic amino group of 2-chloroadenine (18). In addition, HPLC analysis revealed no substantial formation of by-products.

D. Summary of Preparative Methods

Results of preparative examples in addition to those exemplified above in Preparations I, II and III, are summarized in Table 1. Preparative methods typically used approximately molar equivalents of (17) and (18) and calcium hydride and a slight molar excess of base.

TABLE 1

| Solvent‡ | Base* | CaH$_2$ | Time (hrs) | β:α Ratio (19)/(20) | Conversion %† | Isolated Yield (%) |
|---|---|---|---|---|---|---|
| 2:1 tBuOH/DCE | KOtBu | + | 14 | 17 | 54 | ND†† |
| 1:2 DCE/tAmOH | KOtBu | + | 14 | 20.1 | 60 | ND |
| 1:4 DCE/tAmOH | KOtBu | + | 14 | 20.5 | 58 | ND |
| 1:2:2 MeCN/DCE/tAmOH | KOtBu | + | 14 | 22.1 | 74 | ND |
| 52% tBuOH | KOtBu | + | 26 | 10.7 | 90 | 42 |

TABLE 1-continued

| Solvent[‡] | Base* | CaH$_2$ | Time (hrs) | β:α Ratio (19)/(20) | Conversion %[†] | Isolated Yield (%) |
|---|---|---|---|---|---|---|
| 48% MeCN 52% tBuOH | KOtBu | – | 22 | 10.7 | 84 | 77 |
| 48% MeCN 52% tBuOH | KOtBu | – | 21 | 11 | 86 | 79 |
| 48% MeCN 51% amyl alcohol | KOtBu | – | 17 | 13.1 | 80 | 83 |
| 49% MeCN 2:2:1 CH$_2$Cl$_2$:tAmOH:MeCN | KOtBu | + | 85 | 18.7 | 71 | 80 |
| 2:1 tAmOH:MeCN | KOtBu | + | 85 | 12.7 | 70 | 84 |
| 2:1 tAmOH:MeCN | KOtBu | + | 85 | 13.1 | 77 | 89 |
| 2:2:1 CH$_2$Cl$_2$:tAmOH:MeCN | KOtBu | + | 69 | 13.9 | 73 | 41 |
| 2:1 tAmOH:MeCN | K t-amylate | – | 18 | 19.6 | 76 | 80 |
| 1:1 t-AmOH:MeCN | K t-amylate | – | 18 | 13.3 | 79 | 84 |
| 1:2 tAmOH:MeCN | K t-amylate | – | 18 | 6.73 | 92 | ND |
| 2:1:1 tAmOH:MeCN:CH$_2$Cl$_2$ | KOtBu | + | 16 | 20.3 | 79 | 48 |

[‡]tBuOH = t-butyl alcohol; DCE = dichloroethane; tAmOH = t-amyl alcohol; MeCN = acetonitrile.
*KOtBu = potassium t-butoxide.
[†]Conversion % = a.u.c. of (19) + (20)/(18) + (19) + (20) × 100.
[††]ND = not determined.

Example 3

Purification of 2-Chloro-9-(3,5-O-dibenzoyl-2-deoxy-2-fluoro-β-D-arabinofuranosyl)adenine by Re-slurry A re-slurry step utilizing methanol reflux was used to purify compound (19). I necessary, the pH should be adjusted to 6.0 prior to this step to prevent deprotection during the re-slurry step. Given that the re-slurry must involve an equilibrium between the solid and solution phases, a period of time is required for this equilibrium to become established under a given set of experimental conditions. Thus, the times required for equilibration by monitoring the anomeric composition of slurries at different solvent ratios and temperatures were examined. Three salient features became apparent: (1) a hot re-slurry resulted in greater amounts of (19) in the solution at equilibrium; (2) the amount of (19) in solution phase increases over time as equilibrium is approached for the hot re-slurry and decreases over time for a room temperature re-slurry; and (3), equilibrium is essentially achieved at 5 hours under hot or room-temperature re-slurry conditions, although a slight change is observed under room temperature conditions over overnight stirring. The room temperature re-slurry produced a greater anomeric increase. It was concluded that a re-slurry at room temperature, for at least 5 hours, followed by a 1 hour cooling and filtration results in the best recovery and anomeric ration. Results of this method are shown in Table 2 for 20 gm runs undertaken in a 1 L reactor.

TABLE 2

| Conditions[†] | Initial ratio (19)/(20)[‡] | Final ratio (19)/(20) | Mass recovery* |
|---|---|---|---|
| A | 19 | 79 | 62 |
| B | 20 | 39 | 69 |
| B | 24 | 66 | 74 |

[†]Conditions: A: 10 ml MeOH per gram of crude (19), reflux 0.5 hour then room temperature for 19 hours, B: room temperature for 5 days.
[‡]refers to the anomeric ratio going into methanol re-slurry step.
*refers to the mass recovery in the methanol re-slurry step only.

Example 4

Hydrolysis of Condensation Product to Afford 2-Chloro-9-(3',5'-O-dibenzoyl-2'-deoxy-2'-fluoro-β-D-arabinofuranosyl)adenine

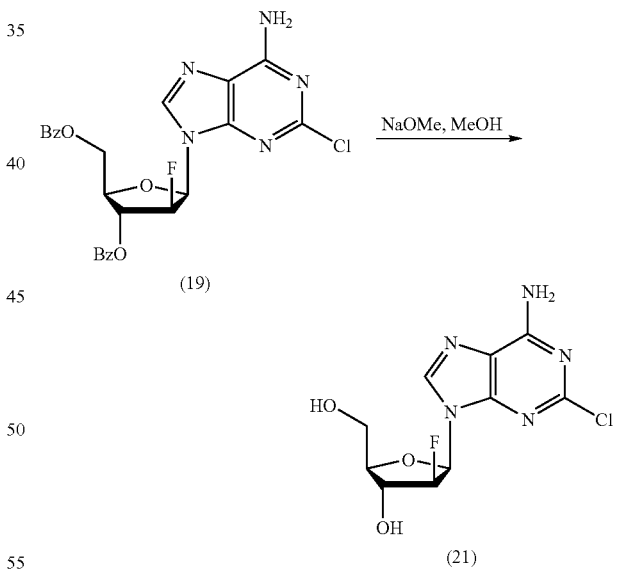

Because methyl benzoate is a liquid and is readily soluble in many organic solvents, cleavage of benzyl groups with sodium methoxide was preferred. A 250 ml, multi-neck flask, equipped with a thermocouple, magnetic stirrer, nitrogen purge and reflux condenser, was charged with (19) (8.42 gm, 16.45 mmol) and 15 ml methanol at ambient temperature. Stirring was started ands the mixture heated to 38° C. The reaction was charged with sodium methoxide (62 μl, 0.329 mmol). The reaction mixture was stirred at 38° C. for 7 hours, heating was them shut off and the mixture cooled to ambient temperature and stirred overnight. The pH was adjusted to 5.0 with acetic acid. The reaction flask was cooled in an ice bath 2 hours and the reaction mixture was filtered and the flask and filtercake were washed with 9.5 ml methanol. The wet solid and 105 ml methanol were charged to a 250 ml, multi-neck flask, equipped with a thermocouple, magnetic stirrer, nitrogen purge and reflux condenser, stirred and heated to reflux. The hot solution was filtered and filtrate transferred to the original reaction flask, wherein the mixture was cooled to ambient temperature. The mixture was cooled in and ice/water bath for 0.5 hour and the mixture filtered and flask and filtercake rinsed with 9.8 ml methanol. The wet solid was dried in a vacuum oven to produced (21) at a yield of 69.4% with a purity of 99.14 (a.u.c.). No α-amoner was detectable by HPLC Further examples of the deprotection method with varying conditions are shown in Table 3.

TABLE 3

| mmol (19) | NaOMe eq. | MeOH mL/g | Temp. °C. | % Mass Recovery | Anomeric Ratio | HPLC Area (%) |
| --- | --- | --- | --- | --- | --- | --- |
| 1.68 | 0.015 | 4 | 25 | 68.8 | 338/1 | 98.0 |
| 2.05 | 0.100 | 20 | 25 | 58.9 | 415/1 | 99.6 |
| 2.11 | 0.010 | 20 | 25 | 58.4 | 469/1 | 93.7 |
| 2.09 | 0.010 | 4 | 25 | 64.2 | 248/1 | 99.0 |
| 2.03 | 0.100 | 4 | 25 | 68.2 | 126/1 | 98.6 |
| 2.82 | 0.055 | 12 | 38 | 60.2 | 330/1 | 99.1 |
| 3.07 | 0.055 | 12 | 38 | 66.9 | 521/1 | 99.0 |
| 2.94 | 0.055 | 12 | 38 | 64.9 | ∞/1 | 99.6 |
| 2.01 | 0.100 | 4 | 50 | 62.6 | 1657/1 | 99.4 |
| 2.07 | 0.010 | 4 | 50 | 64.3 | 521/1 | 98.9 |
| 1.97 | 0.010 | 20 | 50 | 59.3 | 432/1 | 99.4 |
| 1.99 | 0.100 | 20 | 50 | 61.0 | 397/1 | 61.0 |
| 17.05 | 0.020 | 8 | 25 | 53.5 | 988/1 | 98.8 |

Example 5

NMR Designations for Clofarabine and Epi-Clofarabine

Pooled preparations of anomeric mixtures of (19) and (20) were pooled and de-protected by removal of the benzoyl groups by treatment with sodium methoxide and methanol. The resulting clofarabine and epi-clofarabine were isolated by preparative HPLC. In a typical run, 60 mg of crude sample was dissolved in 1.4 mL of the mobile phase, i.e. 1:9 (v/v) acetonitrile/water, for injection onto a Phenomenex Progidy C18, 10μ ODS, 250×21.2 mm column and a flow rate of 12 mL/min. Pooled fractions were rotary evaporated to remove acetonitrile and lyophilized. Purified samples were subjected to NMR analysis.

Figure 2:
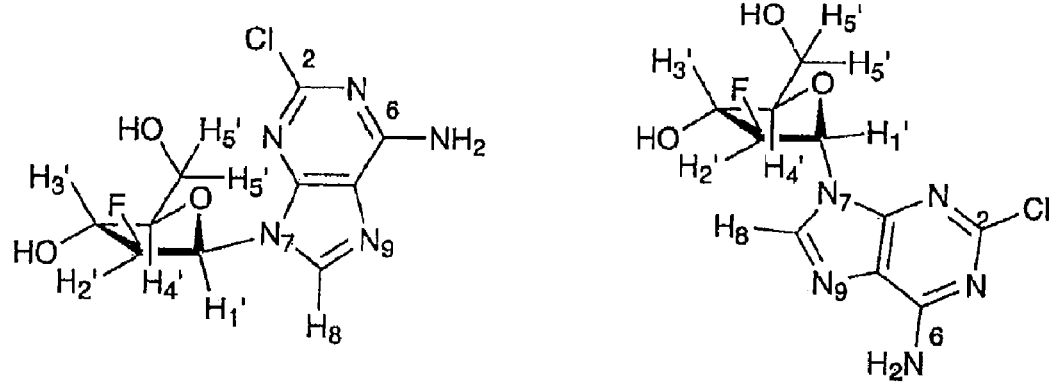
FIG. 2—Schematic of expected conformations of the relevant protons and fluorine atoms for 2-chloro-9-(2'-deoxy-2'-halo-β-D-arabinofuranosyl)adenine (clofarabine) (21) and 2-chloro-9-(2'-deoxy-2'-fluoro-α-D-arabinofuranosyl)adenine (epi-clofarabine) (22).
Figure 2:
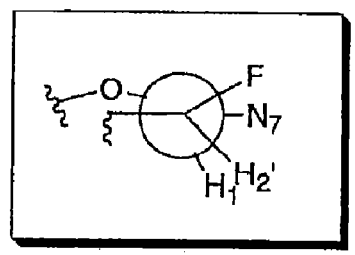
Figure 2:
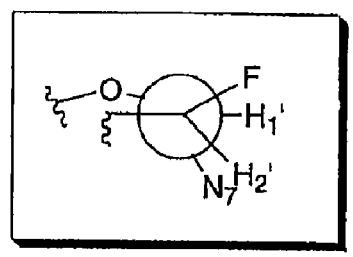

FIG. 2 shows the expected conformations of the relevant protons and fluorine atoms for 2-chloro-9-(2'-deoxy-2'-fluoro-β-D-arabinofuranosyl)adenine (clofarabine) (21) and 2-chloro-9-(2'-deoxy-2'-fluoro-α-D-arabinofuranosyl)adenine (epi-clofarabine):

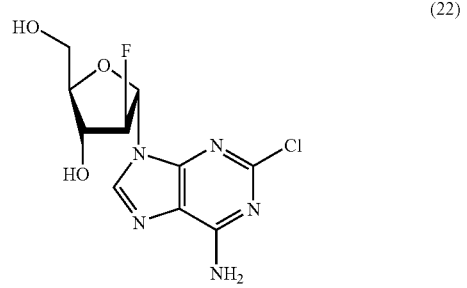

(22)

Figure 3:
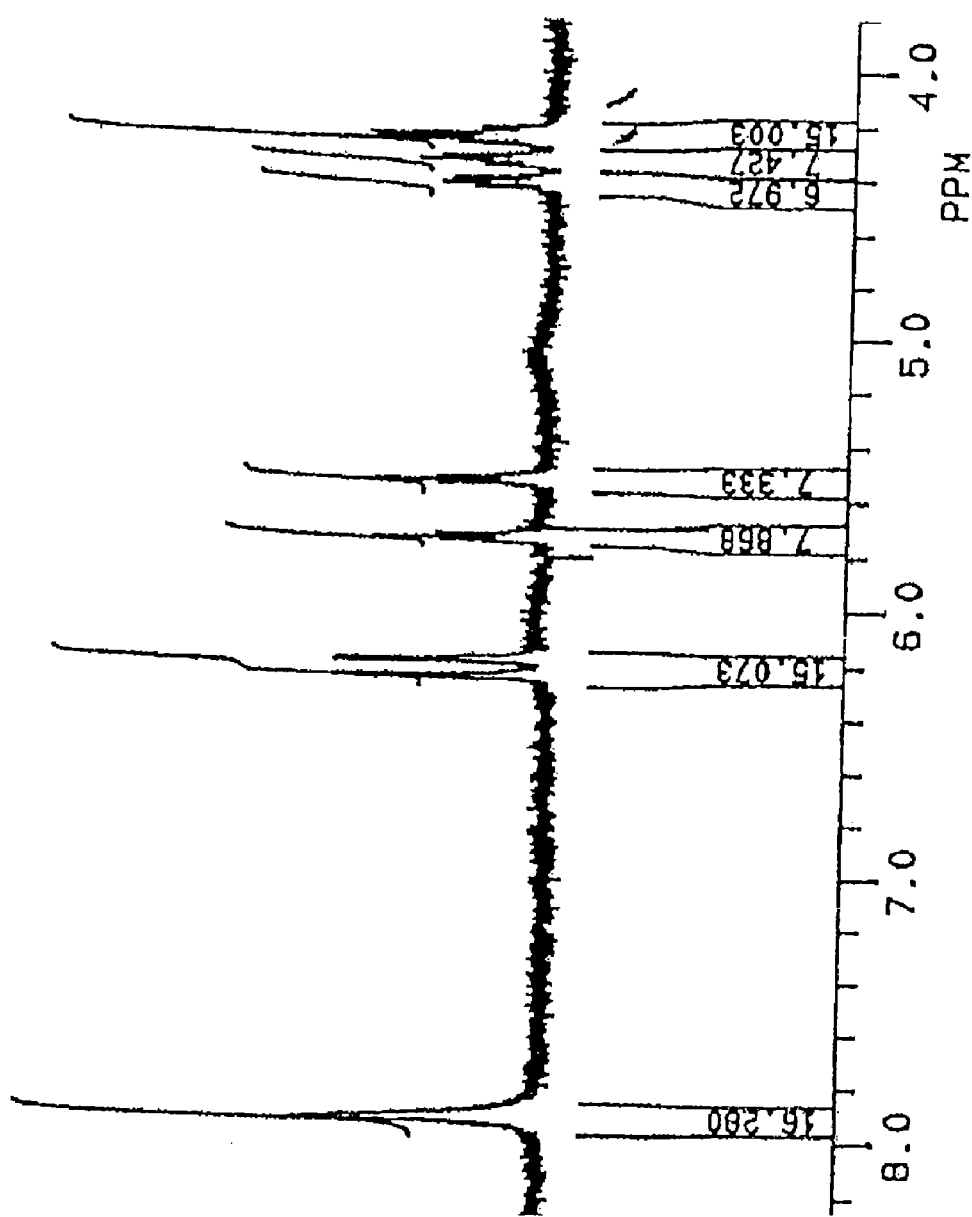
FIG. 3—Partial 1H NMR for 2-chloro-9-(2'-deoxy-2'-fluoro-β-D-arabinofuranosyl)adenine (clofarabine) (21).
Figure 4:
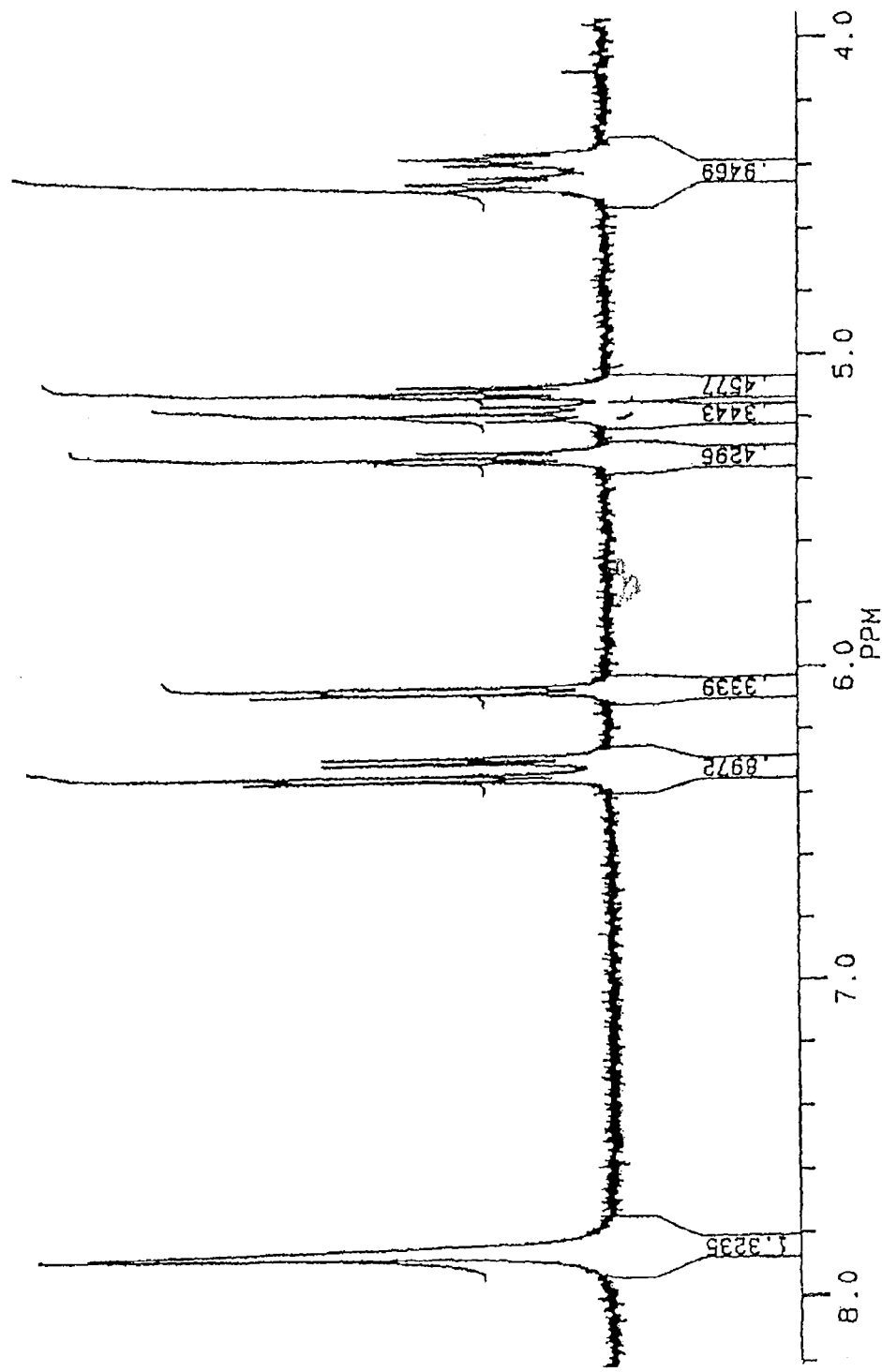
FIG. 4—Partial 1H NMR for 2-chloro-9-(2'-deoxy-2'-fluoro-α-D-arabinofuranosyl)adenine (epi-clofarabine) (22).

Based on these conformational assumptions and the Karpus relationship, the predicted coupling constants of the β-anomer (21) and the α-anomer (22) should conform to the following relationship:
a) $JH_2F$ will be large for both the β or α anomers
b) $(JH_1F)_\beta < (JH_1F)_\alpha$
c) $(JH_1H_2)_\beta > (JH_1H_2)_\alpha$
d) $JH_2H_3$ will be small for both the β or α anomers
These predictions are borne out by the NMR analysis of the purified anomers as shown in Table 2, FIG. 3 and FIG. 4. Notably, the exocyclic $N_6$ protons occur at a predictable chemical shift (7.8-8.0 ppm) for clofarabine (21) and epi-clofarabine (22). Similar $N_6$ chemical shifts were reported for other adenine derivatives (Reid et al., Helv. Chim. Acta, 72:1597-1606, 1989).

TABLE 2

Relevant Chemical Shifts and Coupling Constants for Anomers†

| Compound | $H_2$ δ (ppm) | $H_1$ δ (ppm) |
| --- | --- | --- |
| Clofarabine | 5.76 (dt, 1H, J = 63 Hz, J = 5 Hz) | 6.31 (dd, J = 15 Hz, J = 5 Hz) |
| Epi-Clofarabine | 5.61 (dt, J = 57 Hz, J = 4 Hz) | 6.19 (dd, J = 19.5 Hz, J = 4 Hz) |

†HNMR data collected at 250 MHz in DMSO-d6

The present invention has been shown by both description and examples. The Examples are only examples and cannot be construed to limit the scope of the invention. One of ordinary skill in the art will envision equivalents to the inventive process described by the following claims that are within the scope and spirit of the claimed invention.

What is claimed is:
1. A process for the stereoselective preparation of a 2'-deoxy-β-nucleoside of the formula:

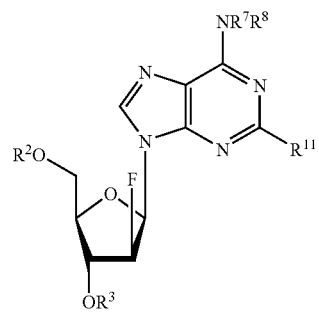

wherein, $R^2$ and $R^3$ are independently hydroxy protecting groups, $R^7$ and $R^8$ are independently hydrogen, $C_1$-$C_4$ alkyl, or amino protecting groups, and $R^{11}$ is a halogen or —$NR^7R^8$, wherein $R^7$ and $R^8$ are as described above, comprising reacting a 2-deoxy-α-arabinofuranosyl derivative of the formula:

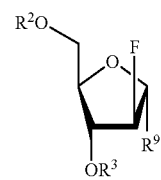

wherein R⁹ is a halogen and R² and R³ are as defined above, with an adenine derivative potassium salt of the formula:

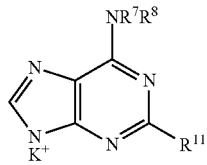

wherein R⁷, R⁸ and R¹¹ are as defined above in the presence of a substantially anhydrous solvent, and wherein said 2'-deoxy-β-nucleoside is produced in said substantially anhydrous solvent in a molar ratio of greater than 10:1 relative to the 2'-deoxy-α-nucleoside anomer represented by the formula:

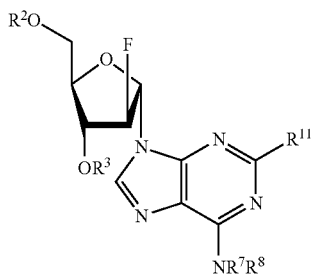

wherein the substantially anhydrous solvent is t-butyl alcohol, acetonitrile, dichloromethane, dichloroethane, t-amyl alcohol, isoamyl alcohol, tetrahydrofuran or mixtures thereof.

2. The process of claim 1, wherein R⁷ and R⁸ are independently hydrogen, R¹¹ is chloro, and R² and R³ are as defined above.

3. The process of claim 2 further comprising de-protecting said 2'-deoxy-β-nucleoside of the formula:

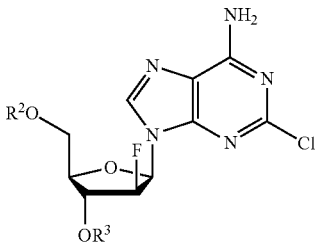

wherein R² and R³ are as defined above to form a 2'-deoxy-β-nucleoside of the formula:

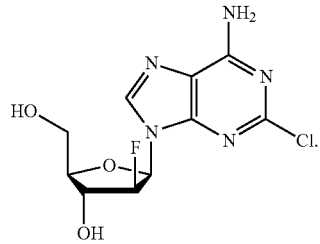

4. A process for the preparation of 2-chloro-9-(2'-deoxy-2'-fluoro-β-D-arabinofuranosyl) adenine comprising:
reacting 3,5-O-dibenzoyl-2-deoxy-2-fluoro-α-D-arabinofuranosyl bromide with a 2-chloroadeinine potassium salt of the formula:

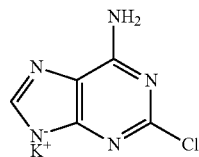

wherein the exocyclic amino group of said 2-chloroadenine potassium salt is not protected, in the presence of a substantially anhydrous solvent selected from t-butyl alcohol, acetonitrile, dichloromethane, dichloroethane, t-amyl alcohol, isoamyl alcohol, tetrahydrofuran or mixtures thereof to form 2-chloro-9-(3',5'-O-dibenzoyl-2'-deoxy-2'-fluoro-β-D-arabinofuranosyl) adenine; and
deprotecting said 2-chloro-9-(3',5'-O-dibenzoyl-2'-deoxy-2'-fluoro-β-D-arabinofuranosyl)adenine to form 2-chloro-9-(2'-deoxy-2'-fluoro-β-D-arabinofuranosyl) adenine.

5. The process of claim 4, wherein the 2-chloro-9-(2'-deoxy-2'-fluoro-β-D-arabinofuranosyl) adenine so formed is substantially pure.

6. The process of claim 5, wherein the ratio of 2-chloro-9-(2'-deoxy-2'-fluoro-β-D-arabinofuranosyl) adenine to 2-chloro-9-(2'-deoxy-2'-fluoro-α-D-arabinofuranosyl) adenine in the 2-chloro-9-(2'-deoxy-2'-fluoro-β-D-arabinofuranosyl) adenine so formed is at least 99:1 as measured by high pressure liquid chromatography and spectrophotometric analysis.

* * * * *